United States Patent [19]
Naf et al.

[11] 4,176,139
[45] Nov. 27, 1979

[54] PROCESS FOR PREPARING UNSATURATED SPIRANIC DERIVATIVES

[75] Inventors: Ferdinand Naf, Geneva; Rene Decorzant, Onex, both of Switzerland

[73] Assignee: Firmenich SA, Geneva, Switzerland

[21] Appl. No.: 934,828

[22] Filed: Aug. 18, 1978

[30] Foreign Application Priority Data

Aug. 26, 1977 [CH] Switzerland ............... 10435/77

[51] Int. Cl.$^2$ ............... C07C 45/00; C07C 49/54
[52] U.S. Cl. ............... 260/586 C; 260/586 G
[58] Field of Search ............... 260/586 C, 586 G

[56] References Cited

PUBLICATIONS

Bahurel et al., "CA" 78:110676t (1973) [C.R. Acad. Sci., Ser. C, 1972, 275(25), 1539–1540].
Bahurel et al., "CA" 81:3442d, (1974) [Synthesis 1974 (2), 118–119].
Descotes et al., "CA", 73:55681k, (1970) [C.R. Acad. Sci. Ser. C, 1970, 270(21), 1735–1738].
Bahurel et al., "CA", 75:88161k (1971) [Bull. Soc. Chem. Fr., 1971, (6) 2209–2214].

*Primary Examiner*—Norman Morgenstern
*Attorney, Agent, or Firm*—Pennie & Edmonds

[57] ABSTRACT

Process for preparing unsaturated spiranic derivatives of formula

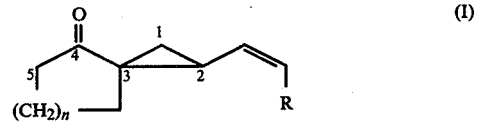

wherein index n represents integer 1 or 2 and wherein symbol R defines a lower alkyl radical, starting from the corresponding cycloalkanone via an addition thereto of a dihalo-alkene of formula

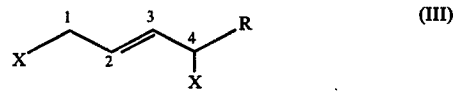

wherein symbol R possesses the above-indicated meaning and X represents a halogen atom.

8 Claims, No Drawings

PROCESS FOR PREPARING UNSATURATED SPIRANIC DERIVATIVES

BACKGROUND OF THE INVENTION

Spiro derivatives of formula (I) are particularly useful intermediates in the manufacture of certain cyclic ketones, eminently interesting in the perfumery field. Examples of these cyclic ketones include cis-jasmone, methyl jasmonate and methyl dihydrojasmonate, whose olfactive properties of flowery, jasmin-like character have gained an increased acceptance in the art. Not surprisingly therefore, the scientific literature is rich in articles reporting processes for their preparation [see e.g.: Parfums, cosmétiques et savons de France, 2,356(1972); Synth. Commun., 4, 265(1974); Parfums, cosmétiques et arômes 1975, [4] 33 and ditto, 1976 [12] 53; Tetr. Letters, 1976, 4867 and the references cited therein].

G. Descotes et al. [Synthesis 1974, 118] have described a process for the preparation of cis-jasmone which process consists in converting a cis-vinyl spiranic ketone into its corresponding cis-diene derivative via the reaction pathway illustrated by the following reaction scheme.

Though original from the scientific viewpoint, the method illustrated above presents serious practical and economical drawbacks, namely in consideration of the cost of certain of the reactants used and of the number of reaction steps actually required. Consequently, the above described method is unsuitable for the large scale industrial manufacture of jasmone.

The process of the present invention is relatively simple procedurally and high yields of the intermediate spiroderivatives of formula (I), and consequently of cis-jasmone, as well as parent derivatives such as methyl jasmonate, are obtained in a rather economic way by making use of cheap commercially available reagents.

THE INVENTION

The invention is concerned with a process for preparing an unsaturated spiro derivative of formula

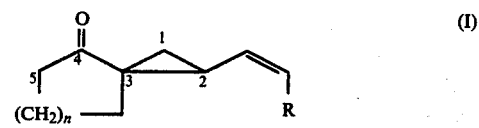

Scheme I

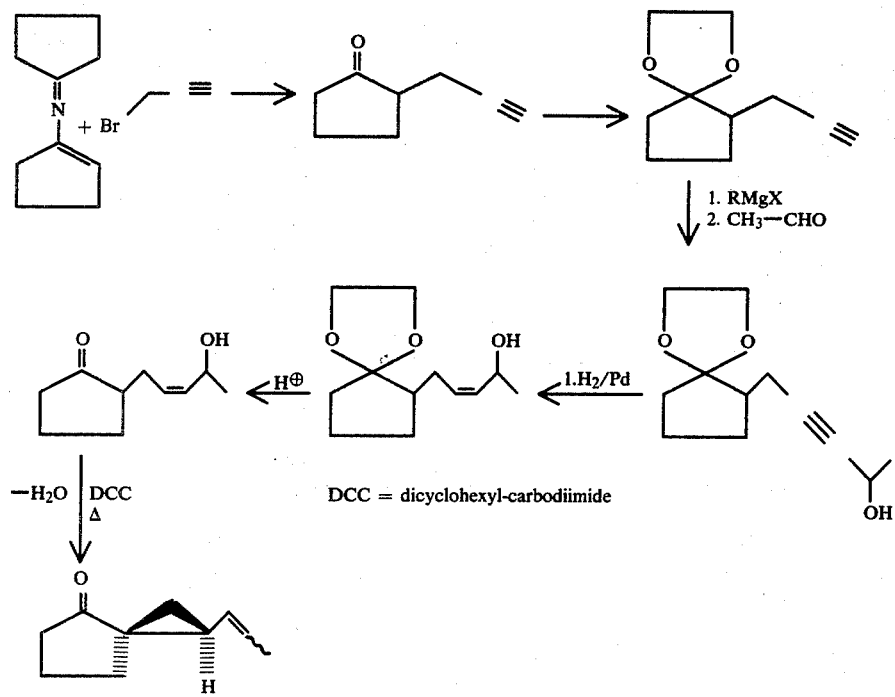

1-(cis-prop-1-en-1-yl)spiro[2.4]heptan-4-one (formula I wherein R=CH₃)

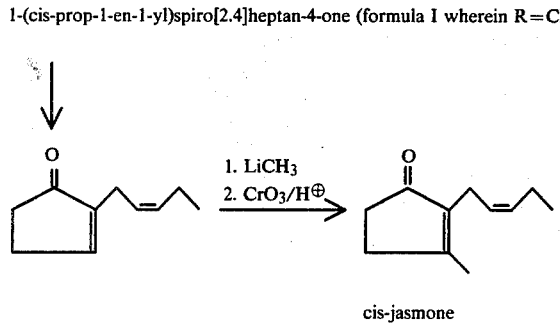

cis-jasmone wherein index n represents interger 1 or 2 and wherein symbol R defines a lower alkyl radical, which comprises treating, in the presence of a strong base, a cycloalcanone of formula

wherein index n has the above given meaning, with a dihaloalkene of formula

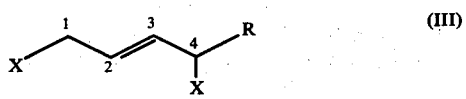

wherein symbol R is defined as above and X represents a halogen atom.

As stated hereinabove symbol R defines a lower alkyl radical. Preferentially, R defines a linear alkyl radical containing from 1 to 3 carbon atoms; methyl radical is more preferred. Symbol X is preferably selected from the group consisting of chlorine, bromine and iodine; bromine is the more preferred halogen atom.

DETAILED DESCRIPTION OF THE INVENTION

It is interesting to observe that in contradistinction to the process described by Descotes, the process of the invention enables to obtain both cis- and trans-isomeric forms of spiro-alcanones (I). The respective structure of these two isomers can be visualized as follows

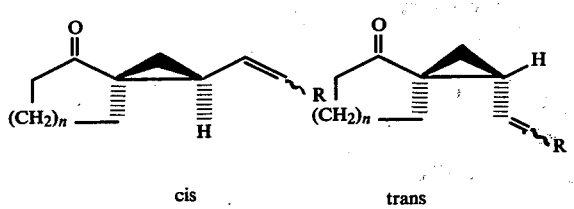

We could establish that said trans isomers undergo conversion into their corresponding 2-(alk-2-cis-en-1-yl)-ketones (see scheme I) more readily and at lower temperature than their corresponding cis derivatives. This represents a supplementary major advantage of the invention process when compared with the prior known process of Descotes.

The reaction which characterizes the process of the invention is promoted by strong bases. Suitable bases include common organic or inorganic bases such as alkali metal-hydroxides, -hydrides, -alkoxides or -amides.

In accordance with a preferred embodiment of the invention, there are used as bases sodium or potassium hydride, sodium amide, or sodium or potassium hydroxide. These latter reagents act preferably in the presence of a phase transfer catalyst [see e.g.: Aldrichimica Acta 9, [3], 35(1976)].

The reaction is effected in the presence of an inert organic solvent, or a mixture of organic solvents or an aqueous organic solvent. Suitable solvents include an ether, an aromatic hydrocarbon or an amide such as dimethylformamide. Tetrahydrofuran, dioxane, benzene and toluene represent the most preferred organic solvents.

The reaction temperature can vary within wide limits, e.g. it ranges between about 0° and 120° C., the temperature however does not play a determining role on the course of the reaction itself. For practical reasons, it is preferred to operate at a temperature value situated in the vicinity of the boiling temperature of the chosen solvent. Thus, by carrying out the reaction in tetrahydrofuran, the preferred temperature is of about 65° C.

Dihalo-compound (III) can be prepared in accordance with usual synthetic techniques, for instance by direct halogenation of a dienic hydrocarbon. In accordance with a preferred embodiment of the process of the invention, 1,4-dibromo-pent-2-ene is used as dihalo-compound (III). This compound can be obtained by bromination of pyperylene in accordance with the method described in J.Org.Chem., 35, 2967(1970). 1,4-Dichloropent-2-ene on the contrary is synthetized according to the procedure described in J.Org.Chem., 41, 334(1976).

The process of the invention is illustrated in a more detailed manner by the following examples wherein the temperatures are indicated in degrees centigrade.

EXAMPLE 1

Vapour phase chromatographic analyses have been carried out on a Carlo Erba, Fractovap GT model by making use of glass columns (230 cm×0.40 cm) packed with 5% SE 30 silicon on Chromosorb W, or with 10% Carbowax on Chromosorb W.

Nuclear magnetic resonance (NMR) spectra have been recorded on a Bruker 4×90/15" spectrometer by analyzing the samples in solution in deuterochloroform.

Mass Spectra (MS) were effected on a Atlas CH$_4$ model spectrometer at an inlet temperature of about 150°; 70 eV. Infrared spectrometer: Perkin-Elmer 125.

1-[Prop-1-en-1-yl)spiro[2.4]heptan -4-one 2.1 g (70 mM) of a 80% suspension of sodium hydride have been washed with anhydrous tetrahydrofuran and mixed then under stirring with 80 ml of tetrahydrofuran (THF) at room temperature during 18 h. 6.6 g (about 20 mM) of 1,4-dibromopent-2-ene (purity about 70%) were added in a single portion to the suspension thus obtained and the whole was brought to the boil.

2.1 g (25 mM) of cyclopentanone, containing 0.3% of water, in 20 ml of THF were added dropwise to the reaction mixture while stirring. After having been left for two supplemental hours at reflux and stirring, the reaction mixture was cooled to room temperature, poured onto ice and extracted with ether. The combined organic extracts were successively washed with 1N HCl, a diluted aqueous solution of sodium bicarbonate and finally water. By the evaporation of the volatile components there were obtained 3.7 g of residue which, upon bulb-distillation gave 2.25 g (yield 67%) of the desired spiro-heptanone having a b.p. of 110°-125°/10 Torr. The assessed purity is of about 90%. The product represents an isomeric mixture containing cis- and trans-1-(prop-1-en-1-yl) spiro [2.4] heptan-4-one in a 2:1 respective weight ratio.

EXAMPLE 2

10.2 ml (ca. 60 mM) of a 23.6% suspension of potassium hydride were washed 3 times with pentane, then suspended in 50 ml THF. 2.1 g (25 mM) of cyclopentanone in 10 ml THF were then added to the obtained KH suspension at room temperature and the reaction mixture was stirred at ca. 20° for 30 min, whereupon it was cooled to 0°. AT this temperature there was added a solution of 6.8 g (21 mM) of 1,4-dibromo-pent-2-ene (purity ca. 70%) in 50 ml THF; this addition was exothermic. The reaction mixture was thus progressively warmed up to ca. 20° and kept under stirring for 30 min., then poured onto ice and extracted with ether. After the usual treatments of neutralisation, washing, drying and evaporation there was obtained 3.52 g of a residue which, by distillation with a bulb apparatus gave 1.93 g of the desired spiro-heptanone, b.p. 80°-115°/0.01 Torr., fraction which was constituted by a 1:1 cis-trans isomeric mixture (purity 81%).

EXAMPLE 3

5.7 g (ca. 18 mM) of 1,4-dibromo-pent-2-ene having a 70% purity have been added at room temperature to a suspension of sodium amide, prepared by dissolving 1.61 g (70 mM) of sodium in 50 ml of liquid ammonia which was then evaporated, in 80 ml of THF. The resulting mixture was heated to reflux and, under vigorous stirring, treated with a solution of 2.1 g (25 mM) of cyclopentanone in 20 ml of THF. Stirring was carried on for 2 h., then the reaction mixture was cooled to room temperature, poured onto ice and extracted with ether. By separation of the organic phases followed by evaporation, there was obtained a residue which, upon distillation by means of a bulb apparatus, gave 1.5 g of a fraction (purity 70%) having b.p. 100°-120°/10 Torr constituted by a 2:1 cis-trans isomeric mixture of 1-(prop-1-en-1-yl)spiro[2.4]heptan -4-one.

EXAMPLE 4

A mixture of 2.1 g (25 mM) of cyclopentanone, 6.8 g (ca. 21 mM) of 1,4-dibromo-pent-2-ene (purity ca. 70%), 1 g of trioctylammonium chloride and 70 ml of a 10% KOH solution in water was kept at 60° under vigourous stirring for 6 h.

The reaction mixture was then cooled to room temperature, then extracted with ether. After separation, the combined organic extracts were subjected to the usual treatment, of washing, drying and evaporation to give at b.p. 90°-105°/0.01 Torr a mixture of cis- and trans- 1-(prop-1-en-1-yl)spiro[2.4]heptan-4-one accompanied by α-cyclopentylidene-cyclopentanone in the respective weight ratio of 1:4:5.

EXAMPLE 5

By carrying out the reaction as indicated in Example 1, and by replacing 1,4-dibromo-pent-2-ene by 1,4-dichloro-pent-2-ene (purity ca. 50%; 6.95 g), there was obtained a mixture (0.59 g; b.p. 90°-120°/10 Torr) containing about 40% of cis- and trans-1-(prop-1-en-1-yl)spiro[2.4]heptan-4-one.

The two cited isomers showed the following analytical characters:

cis 1-(prop-1-en- 1-yl)spiro[2.4]heptan-4-one

NMR(CCl$_4$; 90 MHz): 1.22 (1H, d of d, J$^1$=4 Hz, J$^2$=9 Hz); 1.34 (1H, d of d, J$^1$=4 Hz, J$^2$=6.5 Hz); 1.65 (3H, d of d, J$^1$=5 Hz, J$^2$=1.5 Hz); 5.2-5.7 (2H, m) δ ppm;

IR(CCl$_4$): 1720 cm$^{-1}$.

trans 1-(prop-1-en-1-yl)spiro[2.4]heptan-4-one

NMR(CCl$_4$; 90 MHz): 0.85 (1H, d of d, J$^1$=4 Hz, J$^2$=6.5 Hz); 1.48 (1H, d of d, J$^1$=4 Hz, J$^2$=9 Hz); 1.71 (3H, d of d, J$^1$=6 Hz, J$^2$≃1.5 Hz); 2 (1H); 5.07 (1H, d of d, J$^1$=16 Hz, J$^2$=8 Hz); 5.64 (1H, d of q, J$^1$=16, J$^2$=6 Hz) δppm;

IR(CCl$_4$): 1730 cm$^{-1}$.

What we claim is:

1. Process for preparing an unsaturated spiro derivative of formula

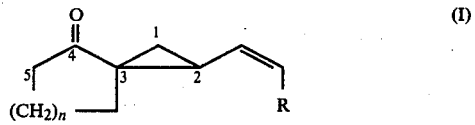

wherein index n represents integer 1 or 2 and wherein symbol R defines a lower alkyl radical, which comprises treating, in the presence of a strong base, a cycloalkanone of formula

wherein index n has the above given meaning, with a dihalo-alkene of formula

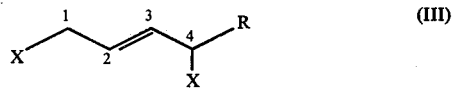

wherein symbol R is defined as above and X represents a halogen atom.

2. Process according to claim 1, which comprises treating cyclopentanone with a 1,4-dihalo-pent-2-ene in the presence of a strong base to give 1-(prop-1-en-1-yl)spiro[2.4]heptan-4-one.

3. Process according to claim 1 or 2, which comprises using as strong base an alkali metal hydroxide, -hydride, -alkoxide or -amide.

4. Process according to claim 3, which comprises using as strong base sodium or potassium hydride in an inert organic solvent.

5. Process according to claim 3, which comprises using an alkali metal hydroxide in the presence of a phase transfer catalyst.

6. Process according to claim 4, wherein the inert organic solvent is tetrahydrofuran.

7. Process according to claim 6, wherein the reaction is carried out at a temperature of about 65° C.

8. Process according to claims 1, 2, 4, 5, 6 or 7 which comprises using as dihalo-alkene, 1,4-dibromo-pent-2-ene.

* * * * *